(12) United States Patent
Shi et al.

(10) Patent No.: US 12,053,550 B2
(45) Date of Patent: Aug. 6, 2024

(54) PREPARATION AND USE OF SUGAR-TARGETING NANOPARTICLES FOR MODIFYING SiRNA

(71) Applicant: HENAN UNIVERSITY, Kaifeng (CN)

(72) Inventors: Bingyang Shi, Kaifeng (CN); Feiyan Zhu, Kaifeng (CN); Meng Zheng, Kaifeng (CN); Yang Liu, Kaifeng (CN)

(73) Assignee: HENAN UNIVERSITY, Kaifeng (CN)

( * ) Notice: Subject to any disclaimer, the term of this patent is extended or adjusted under 35 U.S.C. 154(b) by 521 days.

(21) Appl. No.: 17/110,525

(22) Filed: Dec. 3, 2020

(65) Prior Publication Data

US 2021/0308069 A1 Oct. 7, 2021

(30) Foreign Application Priority Data

Mar. 24, 2020 (CN) .......................... 202010216451.4

(51) Int. Cl.
*A61K 9/51* (2006.01)
*C12N 15/113* (2010.01)

(52) U.S. Cl.
CPC .......... *A61K 9/5123* (2013.01); *A61K 9/5146* (2013.01); *A61K 9/5192* (2013.01); *C12N 15/1137* (2013.01); *C12N 2310/14* (2013.01)

(58) Field of Classification Search
CPC .. A61K 9/5123; A61K 9/5146; A61K 9/5192; C12N 15/1137; C12N 2310/14
See application file for complete search history.

(56) References Cited

FOREIGN PATENT DOCUMENTS

| CN | 106456743 A | 2/2017 |
|----|-------------|--------|
| CN | 108430497 A | 8/2018 |
| CN | 109880021 A | 6/2019 |
| WO | 2005014815 A1 | 2/2005 |
| WO | 2005116212 A2 | 12/2005 |

OTHER PUBLICATIONS

Zhou et al. (Science Advances (Oct. 9, 2020) vol. 6, No. 41 (eabc7031), pp. 1-14). (Year: 2020).*
First search report for CN 202010216451.4, dated Sep. 15, 2020.
Office action for Application No. 202010216451.4, dated Sep. 29, 2020.
Liu, "Sheng Wu Jishu Gailun (Introduction to Biotechnology)", First Edition, ISBN: 978-7-5655-0040-4, Published Sep. 1, 2010, p. 83.
Perrone, et al., "Effect of mofezolac-galactose distance in conjugates targeting cyclooxygenase (COX)-1 and CNS GLUT-1 carrier", European Journal of Medicinal Chemistry, 141, 2017, 404-416.

* cited by examiner

*Primary Examiner* — J. E. Angell
(74) *Attorney, Agent, or Firm* — Billion & Armitage

(57) ABSTRACT

The present disclosure discloses preparation and use of sugar-targeting nanoparticles for modifying siRNA. A sugar-targeting nanoparticle, including targeting nanocarriers, wherein the targeting nanocarriers are formed by linking in sequence a targeting molecule, a first linking compound, a first hydrophilic biomaterial, a second linking compound and a cationic compound through chemical bonds; the first linking compound and the second linking compound both have a carboxyl group; the first linking compound has a maleimido group at the same time, and the targeting molecule is a cycloaldohexose. Providing the cycloaldohexose as the targeting molecule facilitates the nanoparticles targeting the GLUT-1 protein on the capillary endothelial cell membrane on the blood brain barrier, and the nanoparticles are transferred to the brain with high efficiency through the effect of the GLUT-1 protein to transport cycloaldohexose, thereby effectively penetrating the blood brain barrier, and helping to improve the efficiency of sugar-targeting nanoparticles penetrating the BBB.

20 Claims, 5 Drawing Sheets

Specification includes a Sequence Listing.

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1 gaaccaugc gaugcgaau                                                    19
```

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
auucgcaucg cauagguuc                                               19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uucuccgaac gugucacgut t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
acgugacacg uucggagaat t                                            21

PREPARATION AND USE OF SUGAR-TARGETING NANOPARTICLES FOR MODIFYING SiRNA

CROSS-REFERENCE TO RELATED APPLICATION

The present disclosure claims priority of Chinese patent application with the filing number 2020102164514 filed on Mar. 24, 2020 with the Chinese Patent Office, and entitled "Preparation and Use of Sugar-targeting Nanoparticles for Modifying SIRNA", the contents of which are incorporated herein by reference in entirety.

SEQUENCE LISTING

The instant application contains a Sequence Listing which has been submitted electronically in ASCII format and is hereby incorporated by reference in its entirety. Said ASCII copy, created on Jan. 15, 2021 is named 920_028US1_SL.txt and is 1,431 bytes in size.

TECHNICAL FIELD

The present disclosure relates to the technical field of nanoparticle drug loading, in particular to preparation and use of sugar-targeting nanoparticles for modifying siRNA.

BACKGROUND ART

Alzheimer's disease (AD) is a progressive neurodegenerative disease, and more than 40 million people worldwide suffer from Alzheimer's disease. This is the most common neurodegenerative disease related to age, and is characterized by gradual loss of learning, memory and other cognitive functions. Existing approved treatment methods are to use some neurotransmitter modulators, such as memantine consisting of cholinesterase inhibitors and NMDAR antagonists. Although these treatments may provide some relief and comfort to the patients for the symptoms of AD, they do not prevent the progression of the disease itself. This disease severely affects human physical and psychological health and quality of life, and is one of the major medical problems worldwide.

RNA interference (RNAi) is a post-transcriptional gene silencing mechanism with sequence specificity induced by double-strand RNA (dsRNA). An effector molecule of small interfering ribonucleic acid (small interfering RNA, siRNA) RNAi having a length of about 21-23 base pairs induces the generation of gene silencing complexes by RNA in the cell, and degrades mRNA in a sequence-specific manner, thereby reducing the expression amount of target protein. As a drug for treatment of diseases, siRNA has shown a great application prospect, but siRNA as a biologically active nucleic acid substance has defects of poor stability and low absorption rate, naked siRNA is easily degraded by nuclease when entering serum, moreover, siRNA is negatively charged and has strong hydrophilicity, so that it cannot easily penetrate the cell membrane to enter the cytoplasm to exert a high-efficient RNAi effect. Delivery of siRNA is a key bottleneck that determines whether siRNA can be used in clinics, and to design and synthesize a safe and effective siRNA delivery carrier becomes an important direction for the current siRNA drug research and development. Researchers have developed various viral and non-viral delivery carriers so as to improve the efficacy of in vivo RNAi therapy. Viral carriers have higher transfection efficiencies than non-viral carriers, but their association with insertional mutagenesis and immunogenicity limits their use in therapy.

In addition, one of the reasons why Alzheimer's disease cannot be effectively treated is hindrance of blood brain barrier (BBB), and it is difficult for the drug to effectively reach the lesion site, thus the therapeutic effect is unsatisfactory. In order to solve the problems of difficult drug delivery and low drug action efficiency, it is necessary to select a nano-scale delivery carrier capable of penetrating the blood brain barrier and targeting the brain.

Characteristics such as biocompatibility, low toxicity, and extensibility of nanoparticles in biomedicine have attracted extensive attention of researchers. In general, siRNA nanocarriers should be non-toxic and non-immunogenic for systemic administration, with good biocompatibility. The siRNA nanocarriers effectively condense siRNA by electrostatic interaction. In addition to these features, siRNA delivery nanocarriers should provide a better half-life in the blood stream, which can deliver siRNA to target cells/tissues, promote intracellular uptake thereof and subsequent gene silencing, without adverse influence on individual release kinetics and pharmacological effects thereof.

In view of this, the present disclosure is specifically proposed.

SUMMARY

The present disclosure provides a sugar-targeting nanoparticle, including targeting nanocarriers, wherein the targeting nanocarriers are formed by linking in sequence a targeting molecule, a first linking compound, a first hydrophilic biomaterial, a second linking compound and a cationic compound through chemical bonds, wherein the first linking compound and the second linking compound both have a carboxyl group; and the first linking compound has a maleimido group at the same time, and the targeting molecule is a cycloaldohexose.

The present disclosure further provides a sugar-targeting nanoparticle for modifying siRNA, which includes sugar-targeting nanoparticles, wherein targeting nanocarriers in the sugar-targeting nanoparticles are coated around the siRNA, wherein the siRNA is a BACE1 siRNA or an siRNA inhibiting Aβ aggregation;

- a nucleic acid sequence of sense strand of the BACE1 siRNA is as represented by SEQ ID NO. 1, and a nucleic acid sequence of antisense strand of the BACE1 siRNA is as represented by SEQ ID NO. 2.

The present disclosure further provides a method for preparing the sugar-targeting nanoparticle for modifying siRNA according to any one of claims 7-8, comprising:
- incubating the sugar-targeting nanoparticles with the siRNA in mixture, wherein
- the incubation time is 0.5-1.5 h; and
- the incubation is carried out in a buffer solution.

BRIEF DESCRIPTION OF DRAWINGS

In order to more clearly illustrate technical solutions of examples of the present disclosure, accompanying drawings which need to be used in the examples will be introduced briefly below. It should be understood that the accompanying drawings below merely show some examples of the present disclosure, therefore, they should not be considered as limiting the scope, and a person ordinarily skilled in the art still could obtain other relevant drawings according to these accompanying drawings, without using inventive effort.

DETAILED DESCRIPTION OF EMBODIMENTS

Figure 1:
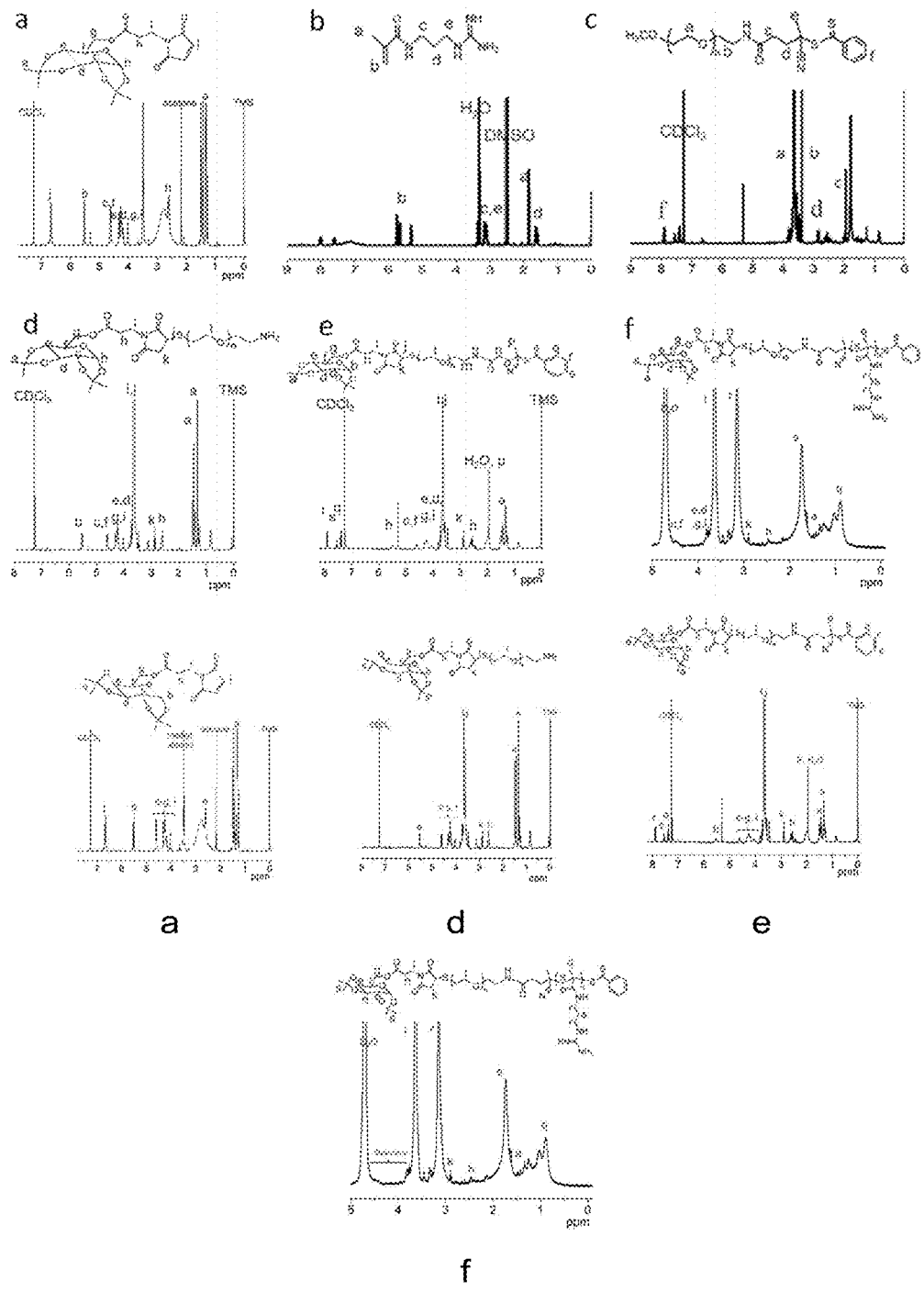
FIG. 1 is a graph of nuclear magnetic resonance analysis of a polymerized intermediate product and a final product prepared in Example 1 and Example 2.

In order to make the objects, technical solutions and advantages of the examples of the present disclosure more clear, the technical solutions in the examples of the present disclosure are described clearly and completely below. If no specific conditions are specified in the examples, they are carried out under normal conditions or conditions recommended by the manufacturer. If manufacturers of reagents or apparatuses used are not specified, they are conventional products commercially available.

An object of the present disclosure is to provide preparation and use of sugar-targeting nanoparticles for modifying siRNA, so as to solve the above technical problems.

The present disclosure is achieved as follows:

a sugar-targeting nanoparticle, including targeting nanocarriers, wherein the targeting nanocarriers are formed by linking in sequence a targeting molecule, a first linking compound, a first hydrophilic biomaterial, a second linking compound and a cationic compound through chemical bonds, wherein the first linking compound and the second linking compound both have a carboxyl group; and the first linking compound has a maleimido group at the same time, and the targeting molecule is a cycloaldohexose.

The targeting nanocarriers are formed by linking in sequence a targeting molecule, a first linking compound, a hydrophilic biomaterial, a second linking compound and a cationic compound through chemical bonds. Providing the cycloaldohexose as the targeting molecule facilitates the sugar-targeting nanoparticles targeting the GLUT-1 protein on the capillary endothelial cell membrane on the blood brain barrier. After 24 hours of starvation, the mice are injected with a glucose solution (20% wt) through the abdominal cavity, to stimulate the GLUT-1 receptor on the blood brain barrier to turn from the outside of blood vessel to the inside of blood vessel, thereby transferring a large amount of sugar-targeting nanoparticles into the brain, so as to effectively penetrate the blood brain barrier, which helps to improve the efficiency of sugar-targeting nanoparticles penetrating the BBB. The first linking compound and the second linking compound are respectively covalently linked to the targeting molecule and the first hydrophilic compound through a carboxyl group.

When the sugar-targeting nanoparticles are loaded with siRNA, it is ensured that the siRNA efficiently reaches the target site, and then exerts medicinal effect. The targeting nanocarriers contain a hydrophilic biomaterial so as to improve the biocompatibility of the sugar-targeting nanoparticles. The first linking compound is provided so as to graft the targeting molecules with the hydrophilic biomaterial. As hydrophilic segment, the cationic compound not only can be used to consequently form a stable nanostructure together with the FPMA, but also can load siRNA through the action of salt bridges, to play a role in loading nucleic acid drugs. In a preferred example of the present disclosure, the cationic compound is GUA.

As a cationic monomer, GUA is N-(3-methylacrylamidopropyl)guanidine chloride, and the hydrophilicity of the targeting nanocarrier can be further improved by ligating the GUA, and thus the compatibility of the targeting nanocarriers is enhanced. The second linking compound is used to graft the hydrophilic biomaterial and GUA. The targeting nanocarriers provided in the above may be used to coat siRNA so as to prepare a therapeutic agent.

In a preferred example of the present disclosure, the cycloaldohexose above is glucose or galactose. By providing glucose or galactose as the targeting molecule, the sugar-targeting nanoparticles are facilitated in targeting the GLUT-1 protein on the capillary endothelial cell membrane on the blood brain barrier, and the sugar-targeting nanoparticles are transferred to the brain with high efficiency through the effect of the GLUT-1 protein to transport glucose or galactose, thereby effectively penetrating the blood brain barrier.

In a preferred example of the present disclosure, the first hydrophilic biomaterial above contains a mercapto group and an amino group. The targeting molecule and the first linking compound are grafted through esterification reaction, the first linking compound is grafted to an end containing mercapto group of the first hydrophilic biomaterial, an amino end of the first hydrophilic biomaterial is linked with the carboxyl end of the second linking compound through dehydration condensation, and the cationic compound is linked with the second linking compound through polymerization.

In a preferred example of the present disclosure, the first linking compound above is maleimidopropionic acid, and the second linking compound is CPADB.

The covalent grafting of the targeting molecule, the hydrophilic biomaterials and the GUA is realized through the chemical linking of various groups above.

In a preferred example of the present disclosure, the first linking compound above is maleimidopropionic acid, and the second linking compound is CPADB. The carboxyl group of the maleimide and the hydroxyl group of the targeting molecule are subjected to esterification, so that the maleimide is grafted on the targeting molecule.

In a preferred example of the present disclosure, the hydrophilic biomaterial above is PEI, polylysine, HS-PHPMA-$NH_2$, HS-dextran-$NH_2$ or HS-PEG-$NH_2$.

In a preferred example of the present disclosure, the hydrophilic biomaterial above is HS-PEG-$NH_2$.

In a preferred example of the present disclosure, the molecular weight of the above HS-PEG-$NH_2$ is 2000. The grafted product and the mercapto group of the hydrophilic biomaterial are subjected to Michael addition reaction, so as to graft the targeting molecule onto the polyethylene glycol. CPADB ($C_{13}H_{13}NO_2S_2$) is purchased from Sigma-Aldrich, and CPADB is subjected to a dehydration condensation reaction with the amino group of HS-PEG-$NH_2$ via the carboxyl group. Further, the product after dehydration condensation is polymerized with GUA to obtain the targeting nanocarrier.

In a preferred example of the present disclosure, the sugar-targeting nanoparticle above further includes non-targeting fluorine-containing nanocarriers, wherein the non-targeting fluorine-containing nanocarriers are linked with the targeting nanocarriers by self-assembling, and the non-targeting nanocarriers are formed by linking in sequence a second hydrophilic biomaterial, a second linking compound, a cationic compound and a hydrophobic block through chemical bonds.

The non-targeting fluorine-containing nanocarriers are obtained by polymerizing the second hydrophilic biomaterial, the second linking compound, the cationic compound and the hydrophobic block by a random copolymerization method.

In a preferred example of the present disclosure, the non-targeting fluorine-containing nanocarriers take fluorine-containing FPMA as a hydrophobic block, with GUA as a hydrophilic and cationic monomer, wherein the non-targeting fluorine-containing nanocarriers with amphipathy have better stability in blood. Self-assembling the non-targeting fluorine-containing nanocarriers and the targeting nanocarriers in water phase according to a certain molar ratio effectively improves the stability of the sugar-targeting nanoparticles, and prolongs the time of the sugar-targeting nanoparticles in blood circulation, so that the sugar-targeting nanoparticles have better half-life period in blood stream, and the effective accumulation of the sugar-targeting nanoparticles in a target site is increased. This facilitates subsequent simultaneous delivery of siRNA and small molecular drugs to target cells/tissues, so that the assembly of the non-targeting fluorine-containing nanocarriers and the targeting nanocarriers not only promotes the prolongation of time in blood circulation, but also increases the accumulation amount in the brain.

In a preferred example of the present disclosure, the second hydrophilic biomaterial above is PEG-NH$_2$, and the second linking compound is CPADB.

In a preferred example of the present disclosure, an end of the second hydrophilic biomaterial above away from the second linking compound is modified with a blocking group.

In a preferred example of the present disclosure, the above blocking group is an alkoxy group.

In a preferred example of the present disclosure, the above blocking group is a methoxy group.

In a preferred example of the present disclosure, the above method for preparing a non-targeting fluorine-containing nanocarrier includes first carrying out dehydration condensation reaction on a hydrophilic biomaterial in the non-targeting fluorine-containing nanocarriers and a second linking compound, and then carrying out copolymerization reaction on the product after the dehydration condensation reaction, the cationic compound and the hydrophobic block. The hydrophobic block is FPMA; and the cationic compound is GUA.

In a preferred example of the present disclosure, the molar ratio of the above product after the dehydration condensation reaction, the GUA and the FPMA added to the copolymerization reaction is 100-110:1800-2000:1.

In a preferred example of the present disclosure, the temperature of the above copolymerization reaction is 60-70° C.

In a preferred example of the present disclosure, the time of the above copolymerization reaction is 24-48 h.

Under the above copolymerization reaction condition, the synthesized target polymer has the highest graft efficiency.

The blocking group is modified so as to prevent the non-targeting nanocarriers from grafting the targeting molecules.

In a preferred example of the present disclosure, the molar ratio of the above targeting nanocarriers to the non-targeting fluorine-containing nanocarriers is 2-5:10.

In a preferred example of the present disclosure, the molar ratio of the above targeting nanocarriers to the non-targeting fluorine-containing nanocarriers is 2.5:7.5.

When the molar ratio of the targeting nanocarriers to the non-targeting fluorine-containing nanocarriers is 2.5:7.5, the prepared sugar-targeting nanoparticles have the highest brain penetrating efficiency.

In a preferred example of the present disclosure, the polymerization degree of GUA is 16-20, and the polymerization degree of FPMA is 2-6 in the above non-targeting fluorine-containing nanocarriers. When the polymerization degree of GUA is 16-20, and the polymerization degree of FPMA is 2-6 in the non-targeting fluorine-containing nanocarriers, the grafting efficiency is the best.

A sugar-targeting nanoparticle for modifying siRNA, which includes sugar-targeting nanoparticles, wherein targeting nanocarriers in the sugar-targeting nanoparticles are coated around the siRNA, wherein the siRNA is a BACE1 siRNA or an siRNA inhibiting Aβ aggregation;

a nucleic acid sequence of sense strand of the BACE1 siRNA is as represented by SEQ ID NO. 1, and a nucleic acid sequence of antisense strand of the BACE1 siRNA is as represented by SEQ ID NO. 2.

The targeting nanocarriers are effectively linked to the siRNA through electrostatic interaction, and coat the siRNA in the sugar-targeting nanoparticles, avoiding that the naked siRNA enters the serum to be easily degraded by nuclease or phagocyted by macrophages, moreover, the targeting nanocarriers are positively charged, so that they easily penetrate the cell membrane to enter the cytoplasm to exert an high-efficient RNAi effect. BACE1 siRNA can specifically perform gene silencing on the BACE1 gene, thereby inhibiting the production and accumulation of β-amyloid protein, thus achieving the treatment of Alzheimer's disease (AD).

In a preferred example of the present disclosure, the sugar-targeting nanoparticle above further includes non-targeting fluorine-containing nanocarriers, and the non-targeting fluorine-containing nanocarriers are linked with the targeting nanocarriers by self-assembling.

In a preferred example of the present disclosure, the molar ratio of the above non-targeting fluorine-containing nanocarrier to the siRNA is 1.5-5:1.

In a preferred example of the present disclosure, the molar ratio of the above non-targeting fluorine-containing nanocarrier to the siRNA is 2.5:1.

When the non-targeting fluorine-containing nanocarriers and the targeting nanocarriers are mixed uniformly in a molar ratio of 3:1, and then incubated with siRNA at a mass ratio of 2.5:1, the prepared sugar-targeting nanoparticles can better load siRNA, and the prepared sugar-targeting nanoparticles maintain a particle size between 120-160 nm, with PDI (polymer dispersibility index) lower than 0.2.

A method for preparing a siRNA-loading sugar-targeting nanoparticle, which includes: incubating sugar-targeting nanoparticles with siRNA in mixture;

or mixing and co-incubating a first agent, a second agent with siRNA;

In a preferred example of the present disclosure, the above incubation time is 0.5-1.5 h.

In a preferred example of the present disclosure, the above incubation is carried out in a buffer solution.

In a preferred example of the present disclosure, the above buffer solution is a Hepes buffer solution.

The Hepes buffer solution is a hydrogen ion buffer, and can control a constant pH range for a relatively long time. In the present example, the pH is controlled to be 7.2-7.4.

In a preferred example of the present disclosure, the above preparation method further includes mixing and self-assembling the non-targeting fluorine-containing nanocarriers, the targeting nanocarriers and siRNA.

By means of mixing and self-assembling, the siRNA is embedded in a random copolymer formed from the non-targeting fluorine-containing nanocarriers and the targeting nanocarriers.

Use of a siRNA-loading sugar-targeting nanoparticle in preparation of an therapeutic agent for Alzheimer's disease.

The above BACE1 siRNA-loading sugar-targeting nanoparticles may be prepared into a therapeutic agent, which specifically performs gene silencing on the BACE1 gene, thereby inhibiting the production and accumulation of β-amyloid protein, thus achieving the treatment of Alzheimer's disease (AD).

A potential advantage of using nanoparticles for preparation of an Alzheimer therapeutic agent includes: it has the ability to improve the pharmacological properties of a drug without changing the structure of the drug molecules, the therapeutic efficacy is enhanced by targeted delivery of drug in a tissue- or cell-specific manner, nanoparticles can deliver drug across a series of biological barriers such as epithelium and endothelium, the nanoparticles may deliver the drug to the intracellular site of action, and the nanoparticles have the ability to deliver therapeutic agents and nucleic acid drugs with different physicochemical properties.

The present disclosure has the following beneficial effects:
the present disclosure provides preparation and use of sugar-targeting nanoparticles for modifying siRNA. The targeting nanocarriers are formed by linking in sequence the targeting molecule, the first linking compound, the hydrophilic biomaterial, the second linking compound and the cationic compound through chemical bonds. Providing the cycloaldohexose as the targeting molecule facilitates the sugar-targeting nanoparticles targeting the GLUT-1 protein on the capillary endothelial cell membrane on the blood brain barrier. The sugar-targeting nanoparticles are transferred to the brain with high efficiency through the effect of the GLUT-1 protein to transport cycloaldohexose, thereby effectively penetrating the blood brain barrier, and helping to improve the efficiency of sugar-targeting nanoparticles penetrating the BBB.

When the sugar-targeting nanoparticles are loaded with siRNA, the targeting nanocarriers are effectively linked to siRNA through electrostatic interaction, and coat the siRNA in the sugar-targeting nanoparticles, avoiding that the naked siRNA enters the serum to be easily degraded by nuclease, moreover, the targeting nanocarriers are positively charged, so that they easily penetrate the cell membrane to enter the cytoplasm to exert an high-efficient RNAi effect. Furthermore, by coated in the targeting nanocarriers, the siRNA is provided with a better half-life in the blood. Providing BACE1 siRNA or siRNA that inhibits AB aggregation can specifically perform gene silencing on the BACE1 gene or the Aβ aggregation related gene, thereby inhibiting the production and accumulation of β-amyloid protein, thus achieving the treatment of Alzheimer's disease (AD). Therefore, the sugar-targeting nanoparticles provided in the above may be used to coat siRNA so as to prepare an AD therapeutic agent.

The features and performances of the present disclosure are further described below in detail in combination with examples.

Example 1

The present example provides a method for preparing a targeting nanocarrier, specifically including the following organic synthesis steps. In the present example, a targeting molecule is galactose (Gal), a first linking compound is maleimidopropionic acid, a second linking compound is CPADB, and a first hydrophilic biomaterial is HS-PEG-NH$_2$.

Structural formulae of dGal and dGal-Mal are as shown below:

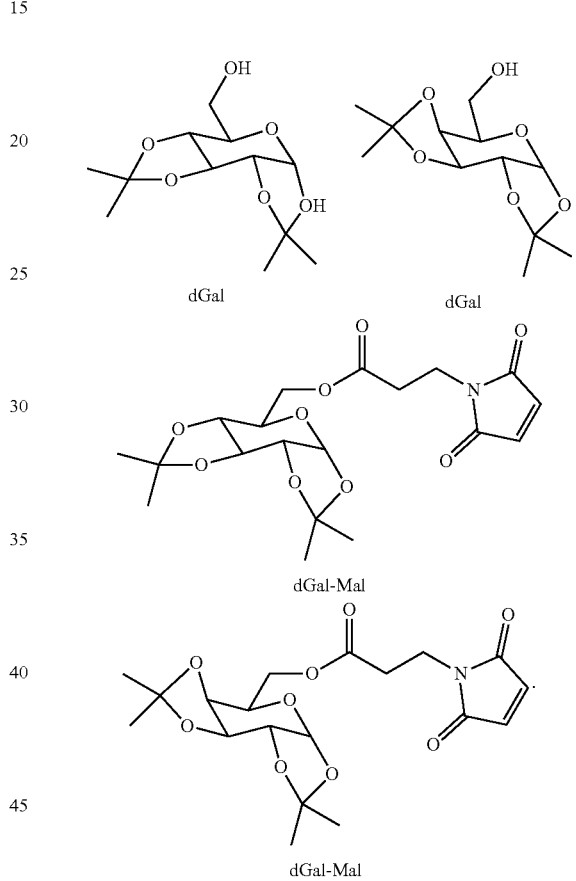

The maleimide was grafted on galactose by esterification of carboxyl group with hydroxyl group through following specific reaction steps: dissolving 3-maleimidopropionic acid (0.50 g, 2.96 mmol) and 1,2,3,4-di-O-isopropylidene-D-α-galactopyranose (0.82 g, 3.15 mmol) in 12 mL of pyridine/dichloromethane solution (1/1=v/v), adding N-ethyl-N'-(3-(dimethylamino)propyl)carbodiimide hydrochloride (EDC·HCl) (0.695 g, 3.62 mmol), N,N-dimethylpyridin-4-amine (DMAP) (19 mg, 0.15 mmol), and stirring the reaction mixture at room temperature for 24 hours, diluting organic phase with dichloromethane (12 mL), washing the resultant with 2M HCl (4×15 mL) and with brine for three times, following by drying over anhydrous sodium sulfate and then concentration to dryness with a rotary evaporator, and obtaining a yellow oily substance, that is, the product Gal-Mal, by being purified by silica gel chromatography (acetone/hexane=1/1v/v; DCM:methanol=1:3). An equation of the synthesis reaction is as follows:

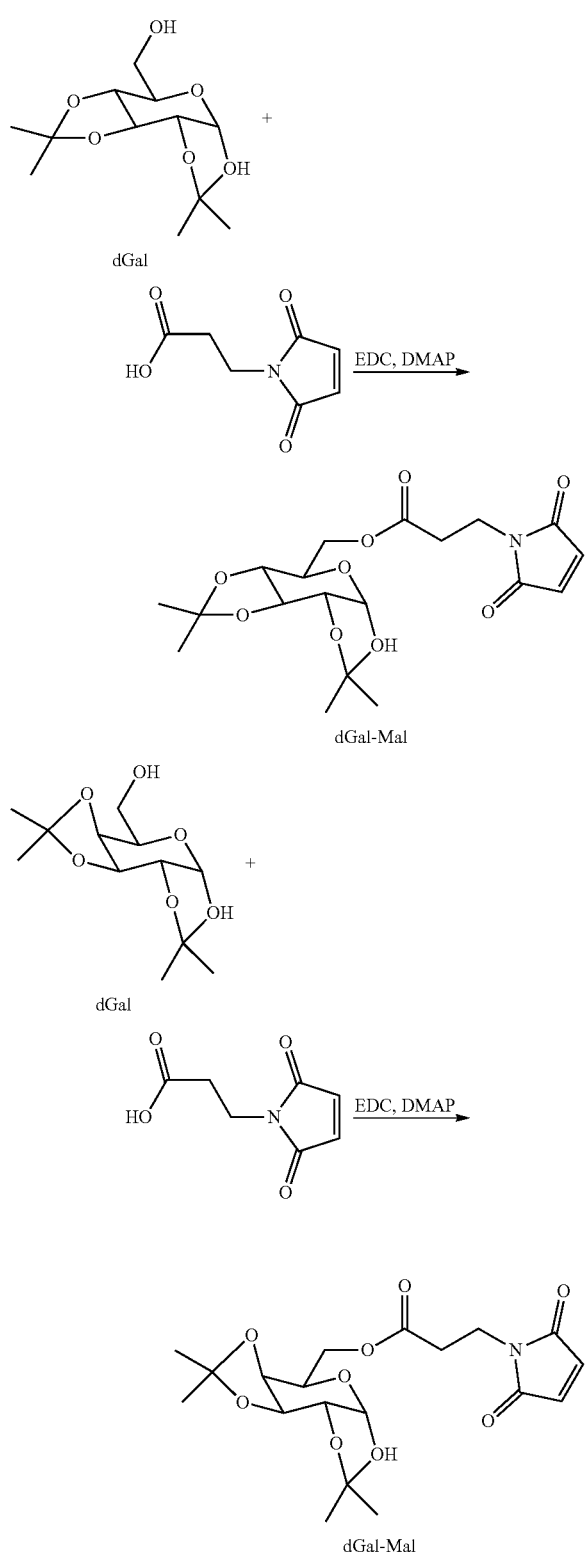

(2) Synthesis of Cationic Monomer (GUA)

The structural formula of N-(3-aminopropyl)methacrylamide hydrochloride (APM) is as follows:

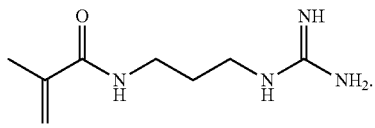

The target monomer GUA was obtained by amino ring-opening reaction through following specific reaction steps: dissolving N-(3-aminopropyl)methacrylamide hydrochloride (APM) (0.50 g, 2.80 mmol), 1H-pyrazole-1-formamidine monohydrochloride (0.41 g, 2.80 mmol) and TEA (0.80 g, 6.7 mmol) in DMF (8 mL), adding hydroquinone (5 mg) as a polymerization inhibitor, stirring the mixture at room temperature in a nitrogen atmosphere for 24 hours, filtering the mixture and then pouring the resultant into diethyl ether (50 mL), precipitating the oily substance obtained, followed by centrifugation (8000 rpm, 5 min, 4° C.) to remove the supernatant, washing the precipitate twice with a solution of acetonitrile (10 mL) and triethylamine (0.5 mL), washing the solid obtained with dichloromethane (15 mL), and then putting the light yellow viscous solid of GUA in a vacuum drying oven to be vacuum-dried to obtain GUA. An equation of the synthesis reaction is as follows:

(3) Synthesis of dGal-HS-PEG (dGal-HS-PEG-NH$_2$)

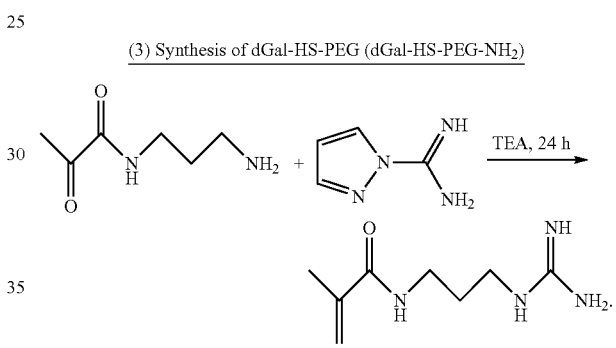

A structural formula of HS-PEG-NH$_2$ is as follows:

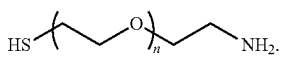

Gal was grafted on polyethylene glycol by Michael addition reaction of Gal-Mal in step (1) with the mercapto group of HS-PEG-NH$_2$, through following specific reaction steps: dissolving dGal-MAL (12.4 mg, 30 umol), HS-PEG-NH$_2$ (Mn=2.0 kg/mol, 50 mg, 25 μmol) in a solution of 2.0 ml of DMSO/PB=1:3, stirring the resultant at room temperature for 24 h, dialyzing the product in ultrapure water (MWCO=500-1000) for one day, followed by lyophilization with a lyophilizer.

An equation of the synthesis reaction is as follows:

(4) Synthesis of dGal-PEG-CPADB.

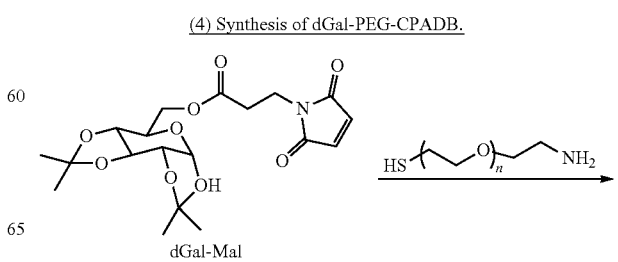

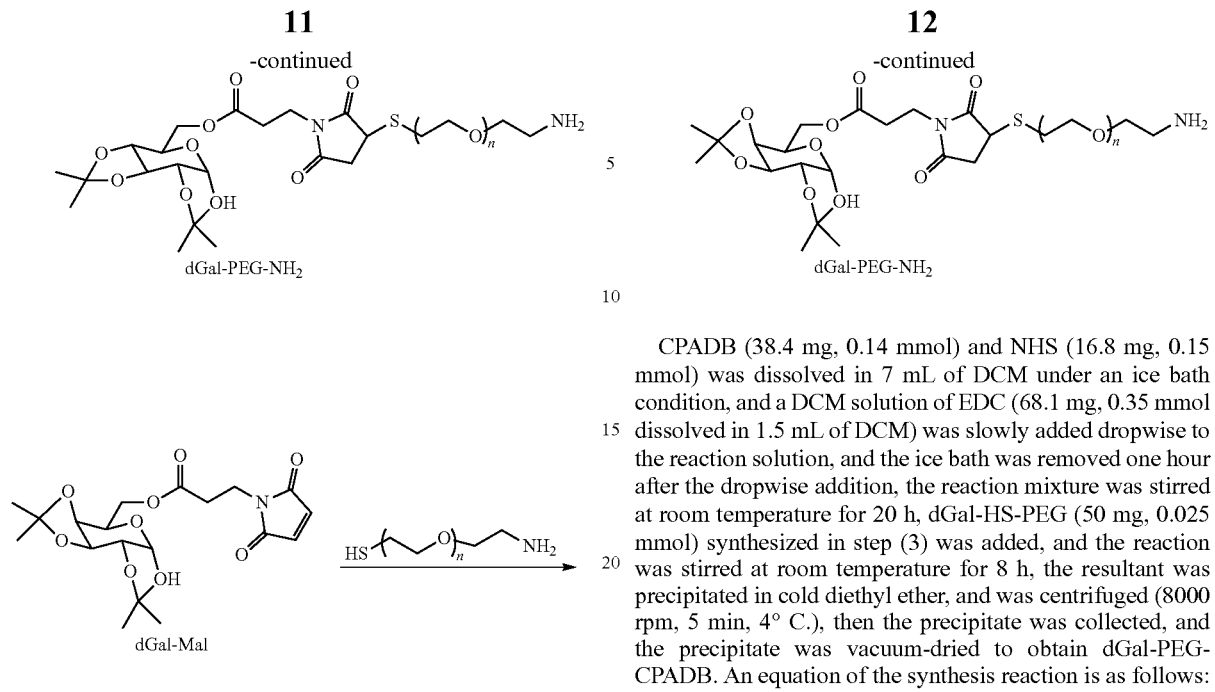

CPADB (38.4 mg, 0.14 mmol) and NHS (16.8 mg, 0.15 mmol) was dissolved in 7 mL of DCM under an ice bath condition, and a DCM solution of EDC (68.1 mg, 0.35 mmol dissolved in 1.5 mL of DCM) was slowly added dropwise to the reaction solution, and the ice bath was removed one hour after the dropwise addition, the reaction mixture was stirred at room temperature for 20 h, dGal-HS-PEG (50 mg, 0.025 mmol) synthesized in step (3) was added, and the reaction was stirred at room temperature for 8 h, the resultant was precipitated in cold diethyl ether, and was centrifuged (8000 rpm, 5 min, 4° C.), then the precipitate was collected, and the precipitate was vacuum-dried to obtain dGal-PEG-CPADB. An equation of the synthesis reaction is as follows:

(5) Synthesis of dGal-PEG-PGUA.

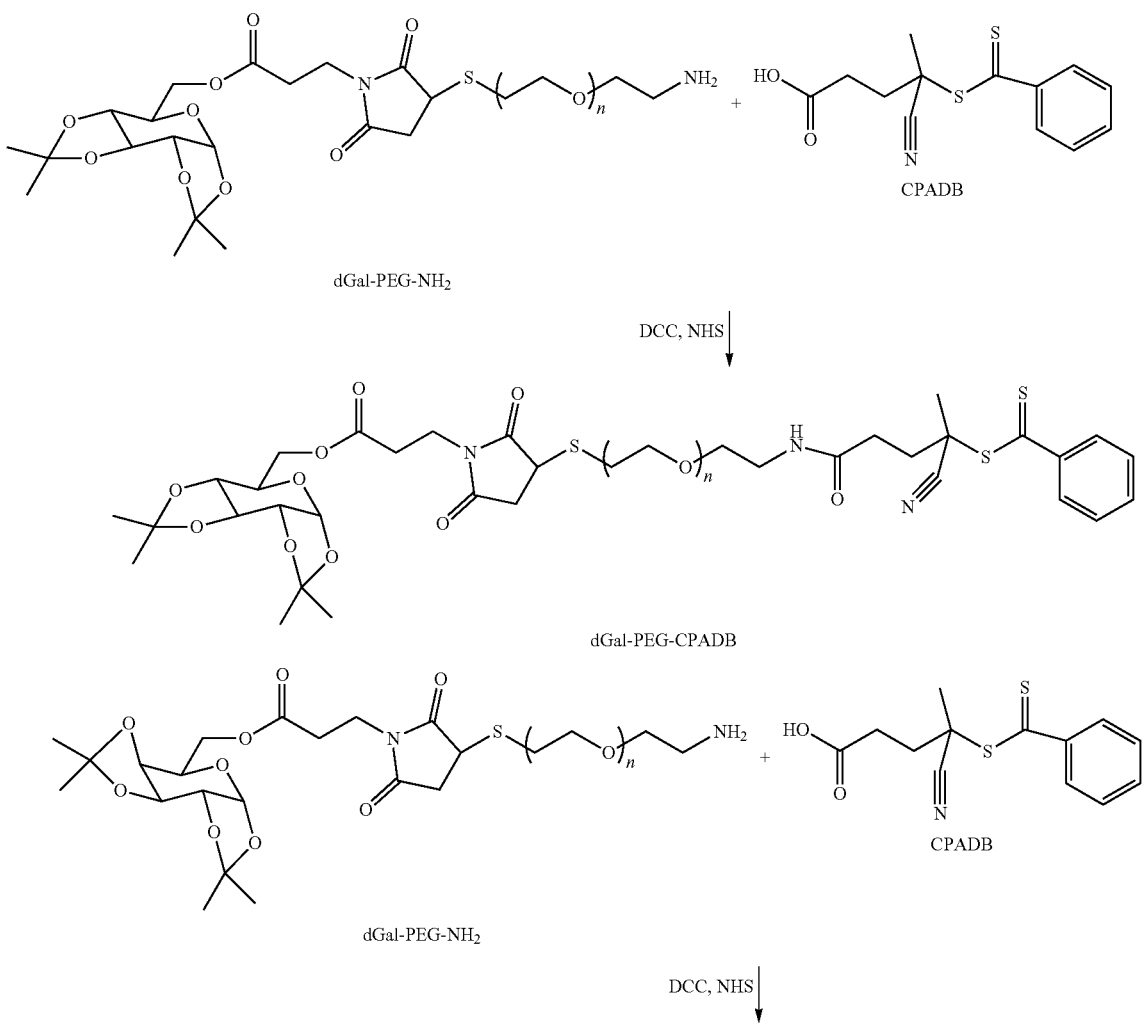

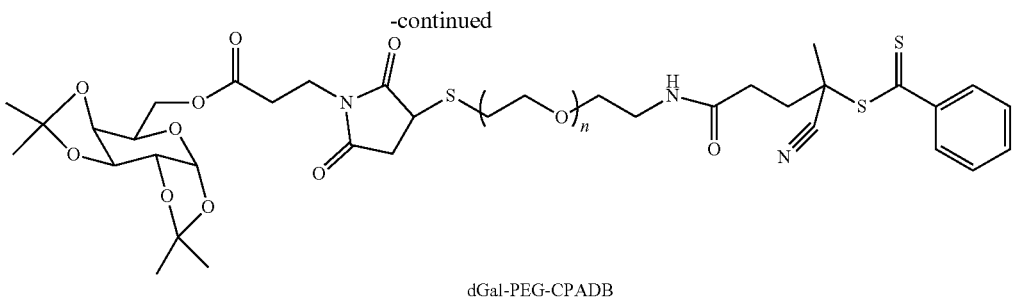

dGal-PEG-CPADB

Nitrogen was introduced in advance into a two-neck flask used in the reaction for 30 min, then GUA (128 mg, 0.58 mmol) synthesized in step (2), Gal-PEG-CPADB (Mn=2.0 kg/mol, 40 mg, 18 μmol) synthesized in step (4) and AIBN (0.52 mg, 6 μmol) were dissolved in 4 mL of DMF, the reaction vessel was sealed and the reaction vessel was immerged in an oil bath at a constant temperature of 65° C., polymerization was carried out for 48 hours, the product Gal-PEG-PGUA was dialyzed in pure water (MWCO=500-1000) for one day, followed by drying with a lyophilizer. An equation of the synthesis reaction is as follows:

(6) Deprotection

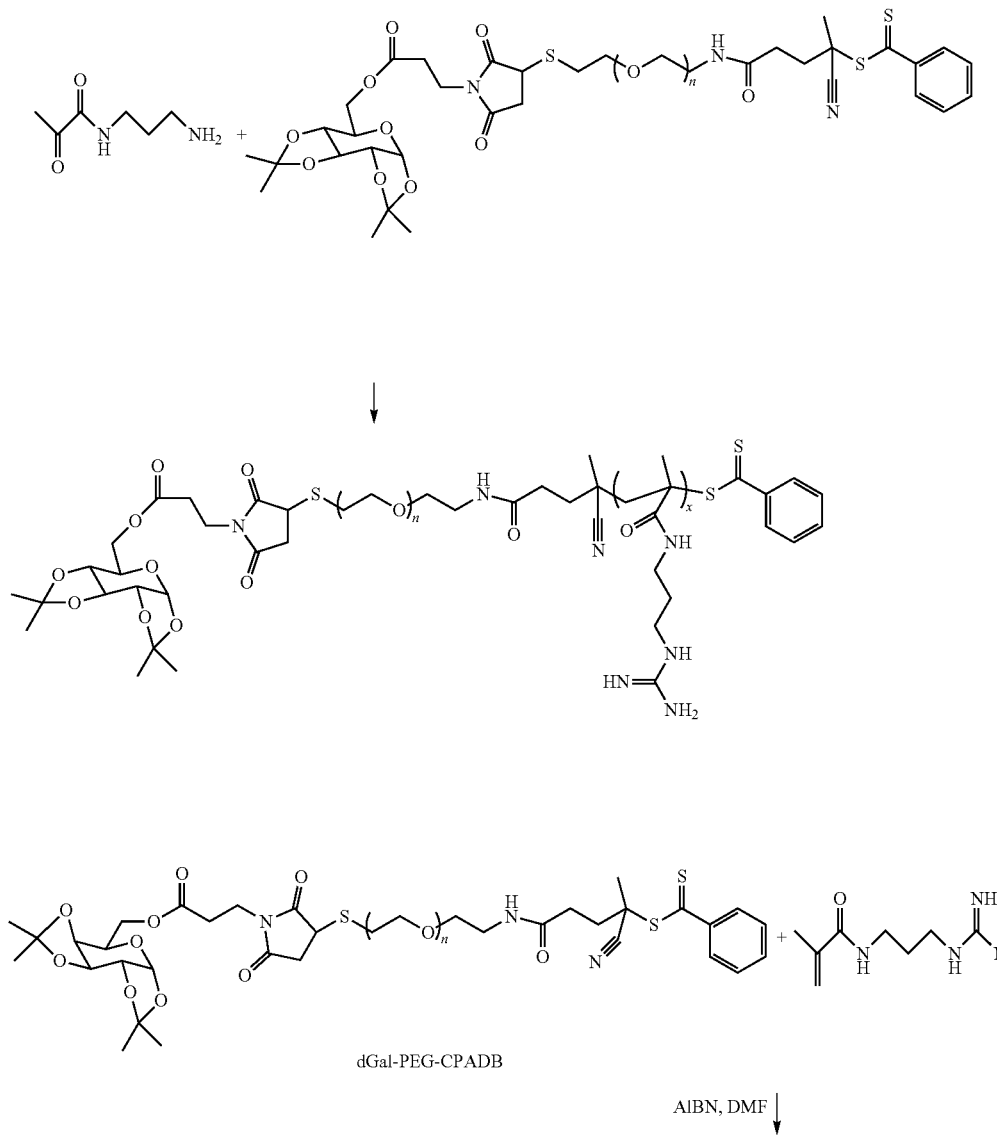

dGal-PEG-CPADB

AIBN, DMF

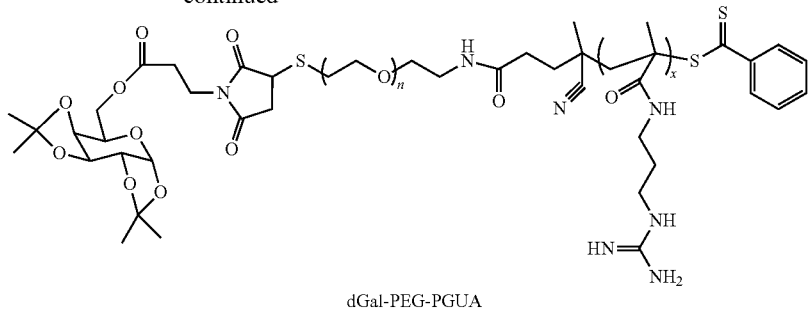
dGal-PEG-PGUA
The polymer dGal-PEG-PGUA (45 mg) was stirred in 80% formic acid (2 mL) at room temperature for 6 h, deionized water (1.5 mL) was added, the mixture is continuously stirred for 3 h, and the solvent was removed under reduced pressure.
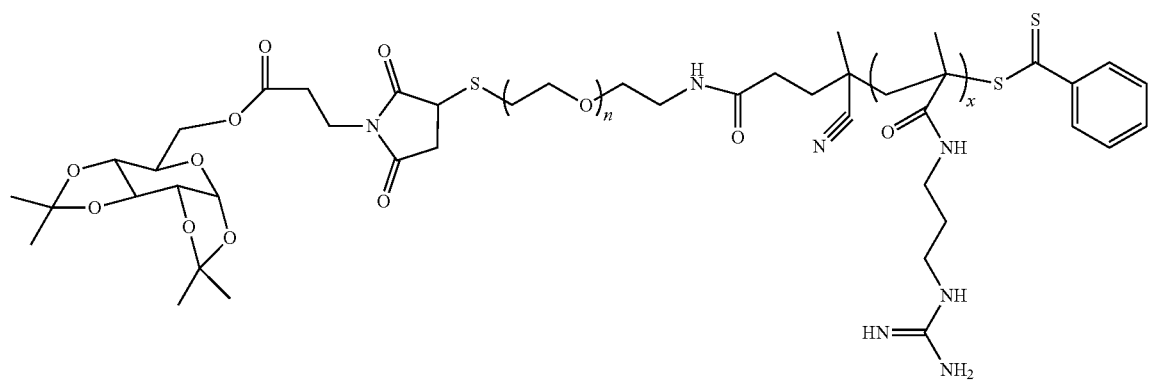
dGal-PEG-PGUA
↓ 80% Formic Acid
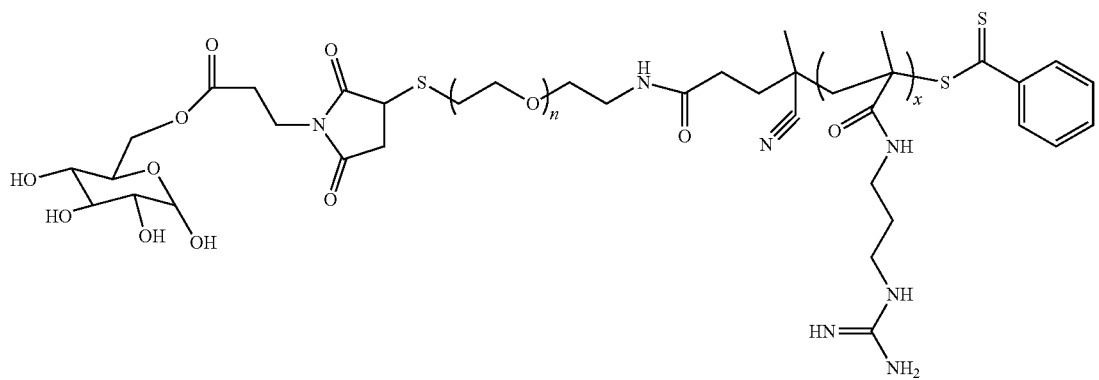
dGal-PEG-PGUA

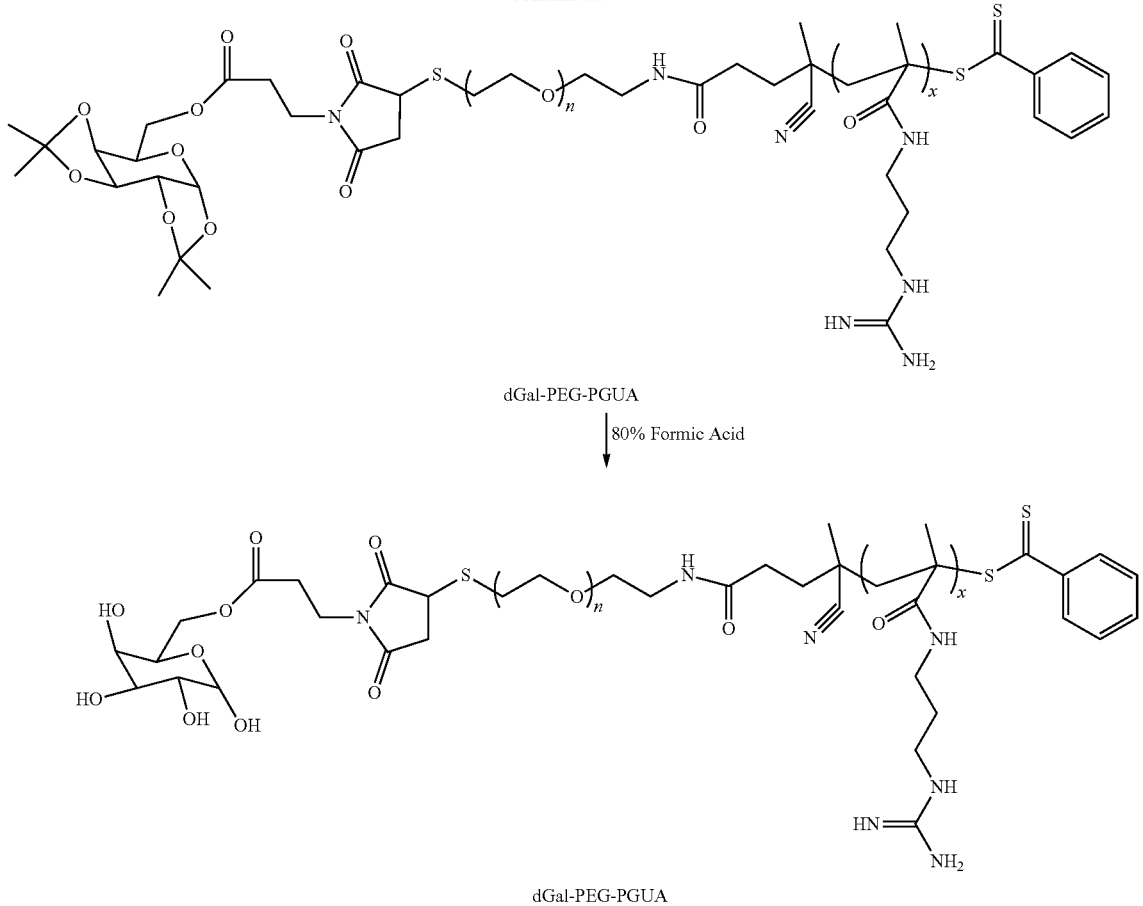

dGal-PEG-PGUA

↓ 80% Formic Acid dGal-PEG-PGUA

Example 2

The present example provides a method for preparing a non-targeting nanocarrier (MeO-PEG-PGUA and MeO-PEG-PGUAF), specifically including the following organic synthesis steps. In the present example, a second linking compound is CPADB, and a second hydrophilic biomaterial is MeO-PEG-NH$_2$.

(1) Synthesis of MeO-PEG-CPADB

CPADB (230.4 mg, 0.696 mmol) and NHS (100.8 mg, 0.852 mmol) was dissolved in 43.8 mL of DCM under an ice bath condition, and a DCM solution of EDC (408.6 mg, 1.986 mmol dissolved in 8.766 mL of DCM) was slowly added dropwise to the reaction liquid, and the ice bath was removed one hour after the dropwise addition, the reaction mixture was stirred at room temperature for 20 hours, MeO-PEG-NH$_2$ (464 mg, 0.232 mmol) was added, and the reaction was stirred at room temperature for 8 hours, the resultant was precipitated in cold diethyl ether, and centrifuged (8000 rpm, 5 min, 4° C.), then the precipitate was collected, and the precipitate was vacuum-dried to obtain MeO-PEG-CPADB. An equation of the synthesis reaction is as follows:

(2) Synthesis of MeO-PEG-PGUA

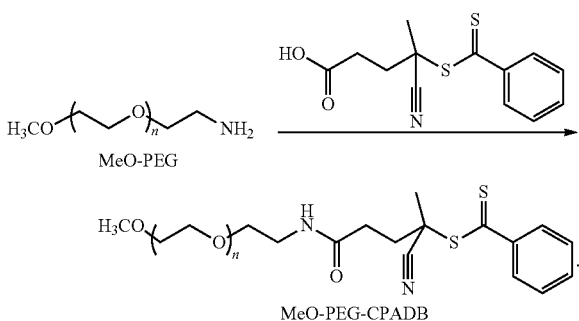

Nitrogen was introduced in advance into a two-neck flask used in the reaction for 30 min, then GUA (128 mg, 0.58 mmol) prepared in step (2) of Example 1, MeO-PEG-CPADB (Mn=2.0 kg/mol, 40 mg, 18 μmol) prepared in step (1) of the present example and AIBN (0.52 mg, 3.2 μmol) were dissolved in 4 mL of DMF, the reaction vessel was sealed and the reaction vessel was immerged in an oil bath at a constant temperature of 65° C., polymerization was carried out for 48 hours, the product MeO-PEG-PGUA was dialyzed in pure water (MWCO=500-1000 Da) for one day, followed by drying with a lyophilizer. An equation of the synthesis reaction is as follows:

(3) Synthesis of MeO-PEG-PGUAF.

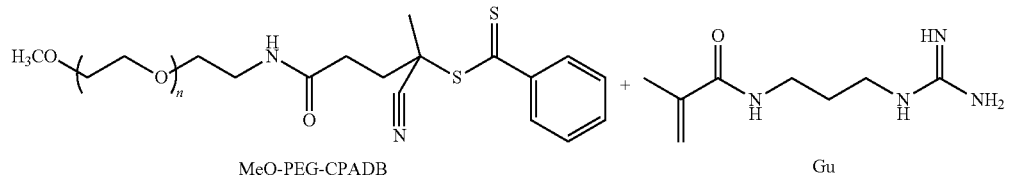

MeO-PEG-CPADB + Gu

AIBN, DMF ↓

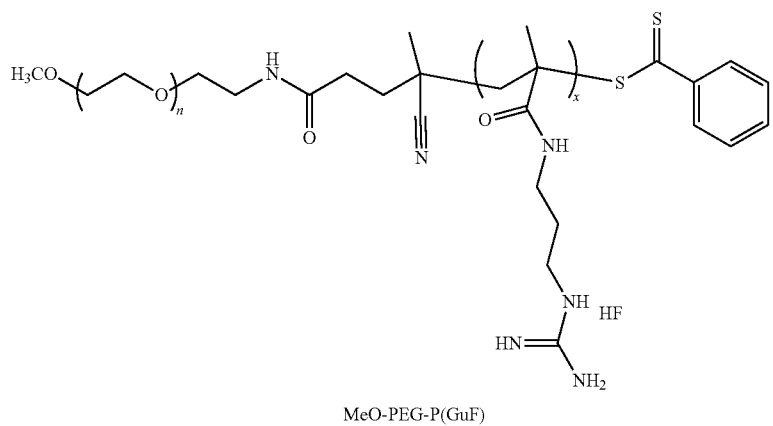

MeO-PEG-P(GuF)

A structural formula of FPMA is as follows:

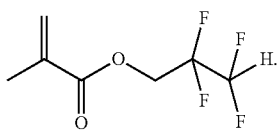

Nitrogen was introduced in advance into a two-neck flask used in the reaction for 30 min, then GUA (44 mg. 0.2 mmol) prepared in step (2) of Example 1, MeO-PEG-CPADB (Mn=2.0 kg/mol, 20 mg, 10 μmol) prepared in step (1) of the present example, FPMA (2,2,3,3-tetrafluoropropyl methacrylate, purchased from Aladdin, CAS No. 45102-52-1, 20 μg, 0.1 μmol) and AIBN (0.26 mg, 1.6 μmol) were dissolved in 2 mL of DMF, the reaction vessel was sealed and the reaction vessel was immerged in an oil bath at a constant temperature of 65° C., polymerization was carried out for 48 hours, and the product MeO-PEG-PGUAF was dialyzed in pure water (MWCO=500-1000) for one day. An equation of the synthesis reaction is as follows:

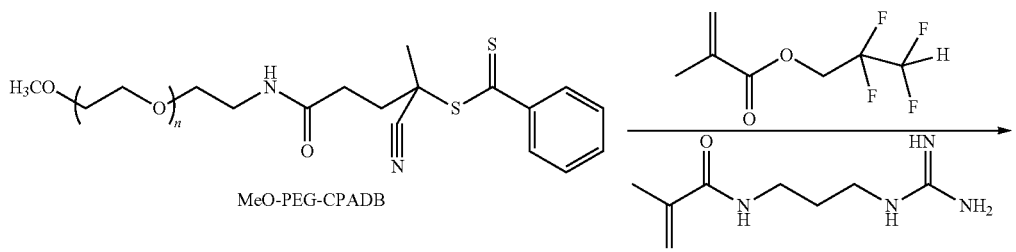

MeO-PEG-CPADB

-continued

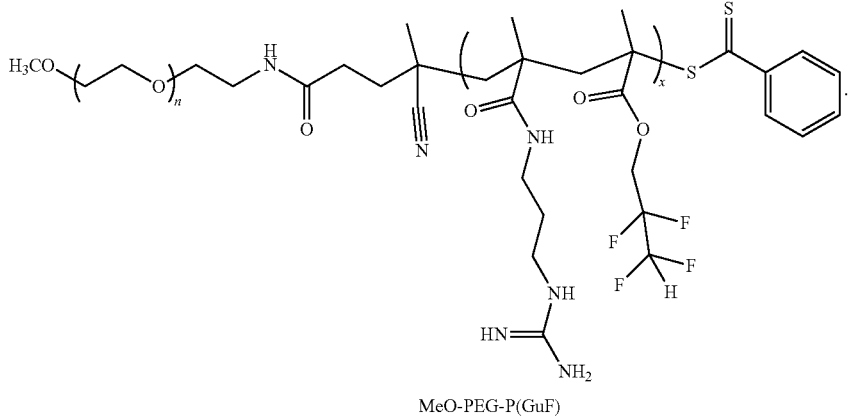

MeO-PEG-P(GuF)

Example 3

The present example provides a method for preparing sugar-targeting nanoparticles for modifying siRNA.

First, siRNA dry powders were centrifuged (7000 rpm, 4 min) to precipitate the siRNA, then 500 μL of DEPC water was added to prepare 1 mg/mL siRNA solution.

Then, the polymer (1 mg, including the targeting nanocarriers prepared in Example 1 and the non-targeting fluorine-containing nanocarriers MeO-PEG-PGUAF prepared in Example 2) was dissolved in 10 mM Hepes buffer solution (pH=7.4, 10 mg/mL), wherein the molar ratio of the targeting nanocarriers to the non-targeting carriers was 1:3, siRNA (15 UM in 10 mM HEPES buffer solution) was added and incubated at room temperature for 1 hour. The sugar-targeting nanoparticles were prepared according to the mass ratio of polymer: siRNA=2.5:1.

Example 4

The present example provides a method for preparing sugar-targeting nanoparticles for modifying siRNA.

First, siRNA dry powders were centrifuged (7000 rpm, 4 min) to precipitate the siRNA, then 500 μL of DEPC water was added to prepare 1 mg/mL siRNA solution.

Then, the polymer (1 mg, the non-targeting fluorine-containing carriers MeO-PEG-GUAF prepared in Example 2 and the targeting nanocarriers Gal-PEG-PGUA) was dissolved in 10 mM Hepes buffer solution (pH=7.4, 10 mg/mL), for subsequent use, and Fluorine-free Gal-NP and Fluorinated Gal-NP were prepared, respectively, siRNA (15 UM in 10 mM HEPES buffer solution) was added and incubated at room temperature for 1 hour. The sugar-targeting nanoparticles were prepared according to the mass ratio of polymer:siRNA=1:1, 2.5:1, 5:1, 10:1, 20:1.

Example 5

The present example provides a method for preparing sugar-targeting nanoparticles for modifying siRNA. The present example is different from the preparation method in Example 3 in that in the present example, the targeting nanocarriers do not carry the targeting molecule, and the remaining preparation steps are the same.

Example 6

The present example provides a method for preparing sugar-targeting nanoparticles for modifying siRNA. The present example is different from the preparation method in Example 5 in that in the present example, siRNA is siScramble sequence, and the remaining preparation steps are the same. The siScramble sequence is control siRNA, which cannot perform silencing.

A nucleic acid sequence of sense strand of the siScramble sequence (as represented by SEQ ID NO. 3) is 5'-UUC UCCGAA CGU GUC ACG UdTdT-3', and a nucleic acid sequence of antisense strand (as represented by SEQ ID NO. 4) is 5'-ACG UGA CAC GUU CGG AGA AdTdT-3'.

Example 7

The present example provides a method for preparing sugar-targeting nanoparticles for modifying siRNA. The present example is different from the preparation method in Example 3 in that in the present example, siRNA is siScramble sequence which is the same as the siScramble sequence in Example 6, and the remaining preparation steps are the same.

Experimental Example 1

Figure 2:
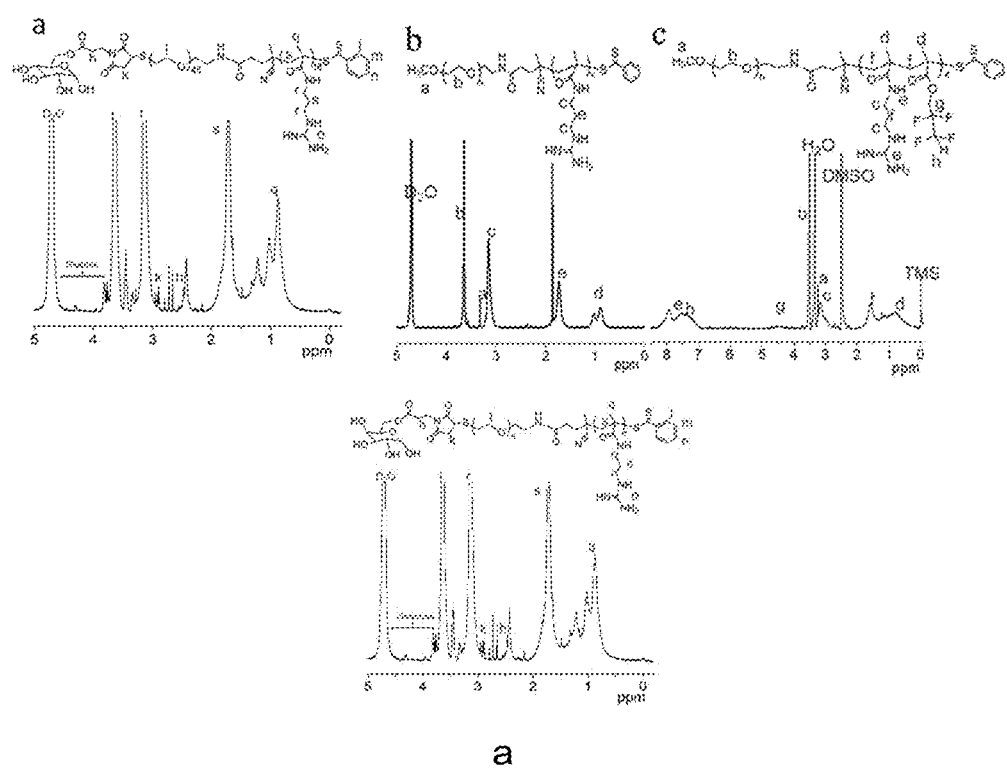
FIG. 2 is a graph of nuclear magnetic resonance analysis of a polymerized intermediate product and a final product in Experimental Example 1.

In the present experimental example, nuclear magnetic resonance analysis was performed on the polymerized intermediate product and the final product prepared in Example 1 and Example 2 with 400 MHz and 16 times of hydrogen spectrum, and the analysis results are shown in FIG. 1 and FIG. 2, wherein drawing a in FIG. 1 shows grafting result of Gal-Mal, drawing b shows a grafting result of a cationic monomer GUA, drawing c is a graph of grafting result of MeO-PEG-CPADB, drawing d is a graph of grafting result of Gal-HS-PEG, drawing e is a graph of grafting result of Gal-PEG-CPADB, and drawing f is a graph of grafting result of Gal-PEG-PGUA. In FIG. 2, drawing a shows grafting result of MeO-PEG-PGUA, and drawing b shows grafting result of MeO-PEG-PGUAF.

Through nuclear magnetic result analysis, the target polymer was successfully synthesized in Example 1 and Example 2, wherein Gal-Mal grafting efficiency was 100%, PEG grafting CPADB efficiency was 97%, polymerization degree of GUA was 16-20, and polymerization degree of FPMA was 2-6.

Experimental Example 2

In the present experimental example, physical property characterization for sugar-targeting nanoparticles was performed on the sugar-targeting nanoparticles for modifying siRNA prepared in Example 4.

(1) The particle size of the sugar-targeting nanoparticles was measured using dynamic light scattering. 100 μL of the incubated nanoparticles were sucked into a measuring dish, and detected at 25° C. Detection results are as shown in FIG. 3, wherein the left diagram in drawing a shows the particle size measurement result (GUA/siRNA) of a siRNA-loaded fluorine-free non-targeting carrier MeO-PEG-PGUA, and the right diagram of drawing a shows the particle size measurement result (GUAF/siRNA) of a siRNA-loaded fluorine-containing non-targeting carrier MeO-PEG-PGUAF.

Figure 3:
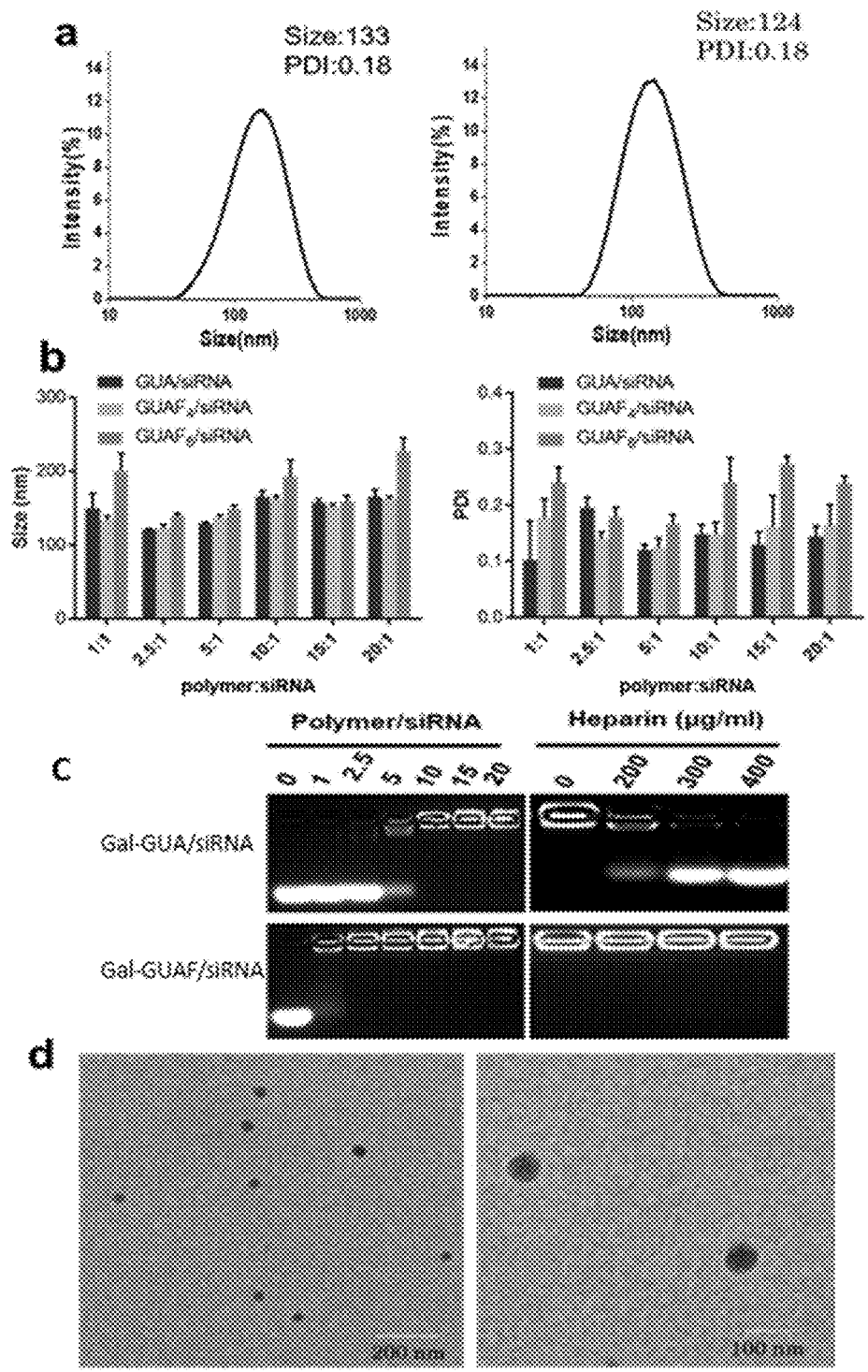
FIG. 3 shows results that siRNA-loaded sugar-targeting nanoparticles prepared in Example 4 are subjected to physical property detection for the sugar-targeting nanoparticles.

It can be seen from the drawing a in FIG. 3 that the particle sizes of GUA/siRNA and GUAF/siRNA is 133 nm and 124 nm, respectively. PDI is less than 0.2.

(2) Polymers of different mass ratios bind to siRNA, and the results of effects on particle size (left diagram) and PDI (right diagram) of fluorine-free non-targeting carrier MeO-PEG-PGUA and fluorine-containing non-targeting carrier MeO-PEG-PGUAF are shown in drawing b in FIG. 3. It can be seen from the drawing b in FIG. 3 that the nanoparticle formed has the particle size of 120-160 nm, and PDI is less than 0.2.

(3) The siRNA binding capability of sugar-targeting nanoparticles by random copolymerization was studied by agarose gel electrophoresis. 2% agarose gel was prepared, the sugar-targeting nanoparticles prepared in Example 4 and the fluorine-free targeting carrier Gal-PEG-PGUA were incubated in a mass ratio of polymer:siRNA=1:1, 2.5:1, 5:1, 10:1, 20:1 for 30 min, and the incubated mixture was fed on a 2% agarose gel, and electrophoresed in TAE solution (40 mM Tris/HCl, 1 v/v % acetic acid and 1 mM EDTA) for 45 min (40 V). A Blue Light Gel Imager (G500312, Sangon Biotech) was used for detection.

The experiment results are shown in drawing c in FIG. 3, and it can be seen from the gel retardation assay that siRNA can be well loaded when the mass ratio of polymer to siRNA is 2.5:1.

(4) The morphology of the sugar-targeting nanoparticles prepared in Example 4 with the mass ratio of polymer:siRNA=2.5:1 was observed by TEM. Results are shown in drawing d in FIG. 3, wherein the sugar-targeting nanoparticles are uniform in morphology under TEM, and have a particle size of about 70 nm.

Experimental Example 3

In the present experimental example, flow cytometry detection and Confocal imaging observation were carried out on the sugar-targeting nanoparticles for modifying siRNA prepared in Example 3 and Example 5.

The flow cytometry detection included following steps: inoculating Neuro-2a cells in a 6-well plate ($1 \times 10^6$ cells/well), adding 2 mL of culture medium for culturing for 24 h, subsequently, sucking away the culture medium, adding the culture medium (200 nm Cy5-siRNA) containing PBS, siRNA, NPs/Cy5 siRNA (i.e. Example 5), and Gal-NPs/Cy5 siRNA (i.e. Example 3), respectively, to incubate at 37° C. for 4 h, and digesting the cells with 0.25% (w/v) trypsin and 0.03% (w/v) EDTA, centrifuging the suspension at 1000 G for 3 min, washing the resultant twice with PBS, and re-suspending in 500 μL of PBS, carrying out the flow cytometry (BD FACS Calibur, Becton Dickinson, USA) test within 1 hour, and circling 10000 cells with Cell Quest software.

The Confocal imaging observation included following steps: inoculating Neuro-2a cells in a 24-well plate ($1 \times 10^5$ cells/well), culturing the cells overnight, adding the culture medium containing PBS, siRNA, NPs/Cy5 siRNA (i.e. Example 5), and Gal-NPs/Cy5 siRNA (i.e. Example 3), respectively, to incubate at 37° C. for 4 h, removing the culture medium, and washing the resultant three times with PBS, fixing the resultant with 4% paraformaldehyde for 15 min, followed by infiltration with 0.1% TRITON X-100 for 15 min, three times of PBS washing, staining with 10 g/ml fluorescent phalloidin for 20-40 min, three times of PBS washing, staining with DAPI (10 μg/mL) for 10 min, and three times of PBS washing. The fluorescence image was obtained using a confocal microscope (TCS SP5, Leica Microsystems CMS GmbH, Germany).

Figure 4:
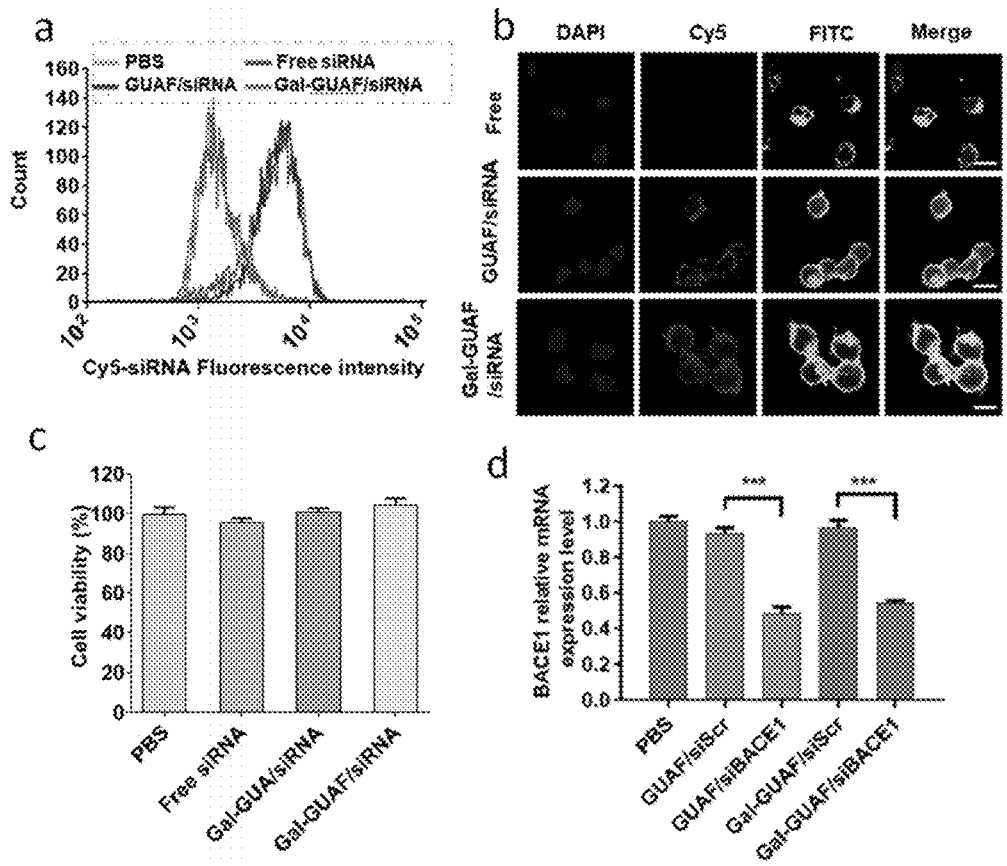
FIG. 4 shows results of flow cytometry detection, Confocal imaging observation, cytotoxicity experiment and in vitro gene silencing experiment for the siRNA-loaded sugar-targeting nanoparticles.

Experimental results are as shown in drawing a and drawing b in FIG. 4, and from the drawing a and the drawing b in FIG. 4, the situation of the sugar-targeting nanoparticles entering the cells can be seen clearly.

Experimental Example 4

In the present experimental example, cytotoxicity experiments and in vitro gene silencing experiments were carried out on the sugar-targeting nanoparticles for modifying siRNA prepared in Example 3, Example 5, Example 6 and Example 7.

The cytotoxicity experiment included the following steps: inoculating Neuro-2a cells in a 96-well plate (6000 cells/well), adding MEM medium (containing 10% fetal bovine serum) to culture the cells for 24 h, thereafter, replacing the culture medium with culture medium (400 nM) containing different nanoparticles and further culturing the cells for 48 h, then adding 20 μL of MTT solution (5 mg/mL), and after 4 h of continuous culturing, removing the culture medium, and adding 150 μL of DMSO, so as to dissolve formazan. The absorbance of each well at 570 nm was detected using an ELIASA, wherein a multifunctional ELIASA was used for measurement. All data show expression relative to untreated control cells (n=3).

In vitro gene silencing experiment included the following steps: studying gene silencing activity of the Bace 1 gene at the cell level using qRT-PCR technology. Neuro-2a cells were inoculated in a 6-well plate ($1 \times 10^6$ cells/well), 2 mL of MEM medium (containing 10% fetal bovine serum) was added to culture the cells for 24 h, the culture medium was sucked away with a pipette, and fresh culture medium (2 mL) containing PBS, GUAF/siScramble (Example 6), GUAF/siBACE1 (Example 5), Gal-GUAF/siScramble (Example 7) and Gal-GUAF/siBACE1 (Example 3) (400 nM siRNA) was added, respectively. After 3 days the cells were washed three times with PBS, and total RNA was extracted with total RNA extraction kit (Tiangen). Reverse transcription was carried out using a reverse transcription kit (takara), and qPCR was measured using the TB Green™ Premix Ex Taq™ (Tli RNaseH Plus) gene expression detection protocol with the LightCycler 480 system. The mRNA expression amount was calculated by AACt method (2-AACt), and the results were expressed by mean standard deviation (n=3).

Experimental results are as shown in drawing c and drawing d in FIG. 4, and it can be seen from the cytotoxicity experiments in drawing c in FIG. 4 that when the siRNA concentration is 400 nmol, the polymer nanoparticles have no toxic and side effects, and it can be seen from the in vitro gene silencing experiment in drawing d that the siBACE1 sequence has a significant silencing effect on BACE1.

Experimental Example 5

Animal experiment was carried out in the present experimental example to explore efficiency of entering brain, half-life and blood glucose changes of the targeting nanoparticles versus the non-targeting nanoparticles.

(1) In in vivo pharmacokinetic studies, 6-8 weeks of BALB/c mice were randomly grouped (3 in each group), 200 μL of Free siRNA, Gal-GUA/Cy5 siRNA (targeting nanocarriers contain no fluorine), and Gal-GUAF/Cy5 siRNA (Example 3) (siRNA has dose of 1 mg/kg) was injected from the tail vein, and blood was taken at a predetermined time point from eye sockets. After blood sampling, each blood sample was immediately dissolved in 0.6 mL of lysis solution (1% Triton X-100), and rapidly dissolved at 37° ° C., and centrifuged (14.8 k rpm, 30 min). The content of Cy5 in the supernatant was determined by fluorimetry. The blood circulation follows a typical two-chamber model, with rapid decline in a distribution phase and a longer elimination phase. We calculated the half-life of the two stages ($t_{1/2}\alpha$ and $t_{1/2}\beta$) by fitting the experimental data, using model: $y=A_1\exp(-x/t_1)+A_2\exp(-x/t_2)+y_0$, then taking $t_{1/2}$, $t_1$, $t_{1/2}\alpha=0.693*t_1$, $\beta=0.693*t_2$.

Figure 5:
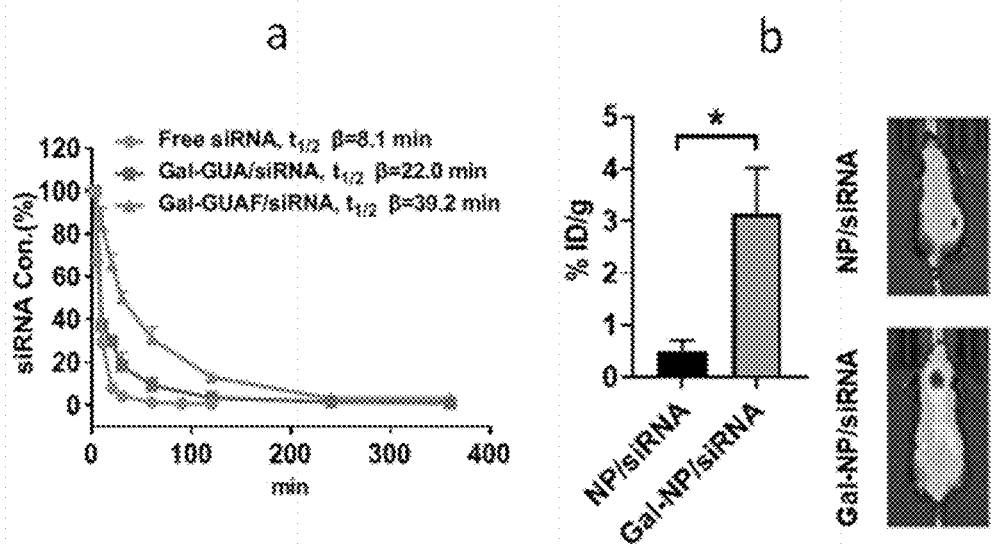
FIG. 5 is a graph of pharmacokinetic and biodistribution results.

Experimental results are as shown in drawing a in FIG. 5, and the pharmacokinetic results indicate that FPMA-containing nanoparticles may greatly increase the blood circulation time of the nanoparticles.

(2) Biodistribution

After fasting for 24 hours, C57 mice were intraperitoneally injected with 20% wt glucose solution, and after half an hour, the C57 mice were injected with nanomedicine through tail vein and then sacrificed after 1 h. The main organs such as heart, liver, spleen, lung, kidney, and brain were taken, washed, dried, and weighed, then dissolved in 0.6 mL of lysis solution (1% Triton X-100), homogenized at room temperature for 4 min, and centrifuged (14.8 k rpm, 30 min) to obtain a supernatant. Cy5 in the supernatant was measured by fluorimetry from a calibration curve and expressed as the injected dose per gram of tissue (% ID/g).

Experimental results as shown in drawing b in FIG. 5, wherein the targeting nanoparticles and the non-targeting nanoparticles are significantly different in the efficiency of entering brain.

Experimental Example 6

Behavioral experiment of mice was carried out in the present experimental example.

a. Water Maze Experiment

Training: the mice were put into water with head facing towards the wall of the pool, and one of four starting positions, namely, east, west, south and north was randomly taken as the position for putting the mice. The time (s) of the animals found an underwater platform was recorded. In the first few times of training, if the time exceeded 60 s, the animals were directed to the platform. The animals were allowed to stay on the platform for 10 s. Each mouse was trained for 4 times every day, with an interval of 15-20 min between two times of training, and the training continued for 5 days.

Probe test: the next day after the training, the platform was removed, and 60 s of probe training was started. The animals were put into water from an opposite side of the original platform quadrant. The time the animals spent in the target quadrant (the quadrant where the platform was originally put) and the number of entries of the animals into this quadrant were recorded as a detection measure of spatial memory.

Reversal training: the working memory of the animals was measured. The next day after the probe training was ended, reversal training was started and continued for 4 days. The platform was placed in the quadrant opposite to the quadrant where the platform was originally placed, with the same method as 1. Training was performed 4 times a day. The time to find the platform, swimming distance and swimming speed were recorded each time.

Reversal probe test: the reversal probe test was carried out the next day of the last reversal training. The method was similar to 2. The time it took for the animals to stay in the target quadrant (the zone where the platform was located the second time) and the number of entries of the animals into this zone within 60 s were recorded.

Figure 6:
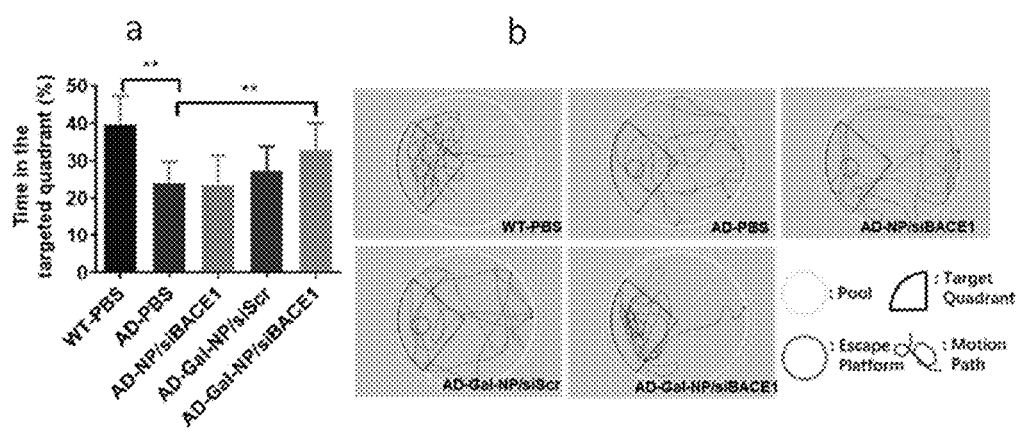
FIG. 6 is a graph of behavioral experimental results of mice.

Experimental results are as shown in FIG. 6, and it can be seen from drawing a and drawing b of the water maze experimental results that after the platform was removed, the retention time of the AD mice in the target group in the target quadrant is significantly different from that of the mice in other groups, with notable improvement on memory, but the other control groups have no improvement compared with the PBS group of the AD mice. In each group n=6.

The above-mentioned are merely for preferred examples of the present disclosure, but are not used to limit the present disclosure. For one skilled in the art, various modifications and changes may be made to the present disclosure. Any amendments, equivalent replacements, improvements, and so on, within the spirit and principle of the present disclosure, should be covered by the scope of protection of the present disclosure.

What is claimed is:

1. A sugar-targeting nanoparticle, comprising targeting nanocarriers, wherein the targeting nanocarriers are formed by linking in sequence a targeting molecule, a first linking compound, a first hydrophilic biomaterial, a second linking compound and a cationic compound through chemical bonds, wherein the first linking compound and the second linking compound both have a carboxyl group; the first linking compound also has a maleimido group; the targeting molecule is a cycloaldohexose; the first hydrophilic biomaterial contains a mercapto group and/or an amino group; the targeting molecule and the first linking compound are grafted through esterification reaction, an amino end of the first hydrophilic biomaterial is linked with a carboxyl end of the second linking compound through dehydration condensation, and the cationic compound is linked with the second linking compound through polymerization, wherein the second linking compound is

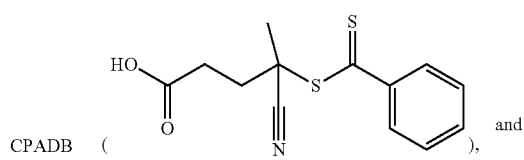 [SMILES: CC(C#N)(CCC(=O)O)SC(=S)c1ccccc1]

and the cationic compound is

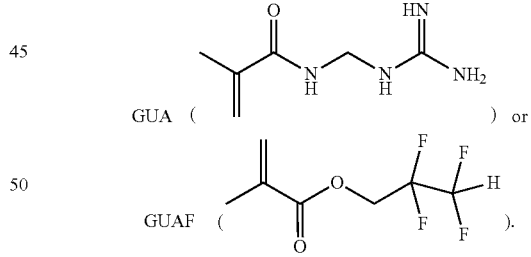

2. The sugar-targeting nanoparticle according to claim 1, wherein the cycloaldohexose is glucose or galactose.

3. The sugar-targeting nanoparticle according to claim 1, wherein the first hydrophilic biomaterial contains a mercapto group and an amino group.

4. The sugar-targeting nanoparticle according to claim 3, wherein the first hydrophilic biomaterial is PEI, polylysine or HS-PEG-NH2.

5. The sugar-targeting nanoparticle according to claim 1, wherein the sugar-targeting nanoparticle further comprises non-targeting nanocarriers, wherein the non-targeting nanocarriers are linked with the targeting nanocarriers by self-assembling, and the non-targeting nanocarriers are formed by linking in sequence a second hydrophilic biomaterial, a second linking compound, a cationic compound and a hydrophobic block through chemical bonds.

6. The sugar-targeting nanoparticle according to claim 5, wherein the sugar-targeting nanoparticle further comprises non-targeting fluorine-containing nanocarriers, and a molar ratio of the targeting nanocarriers to the non-targeting fluorine-containing nanocarriers is 2-5:10.

7. A sugar-targeting nanoparticle for modifying siRNA, comprising the sugar-targeting nanoparticle according to claim 1, wherein the targeting nanocarriers in the sugar-targeting nanoparticle are coated around the siRNA,
wherein the siRNA is BACE1 siRNA or siRNA inhibiting Aβ aggregation,
wherein a nucleic acid sequence of a sense strand of the BACE1 siRNA is represented by SEQ ID NO. 1, and a nucleic acid sequence of an antisense strand of the BACE1 siRNA is represented by SEQ ID NO. 2.

8. The sugar-targeting nanoparticle for modifying siRNA according to claim 7, wherein the sugar-targeting nanoparticle further comprises non-targeting fluorine-containing nanocarriers, wherein the molar ratio of the targeting nanocarriers to the non-targeting fluorine-containing nanocarriers is 2-5:10.

9. A method for preparing the sugar-targeting nanoparticle for modifying siRNA according to claim 7, comprising:
incubating the sugar-targeting nanoparticles with the siRNA in mixture, wherein
the incubation time is 0.5-1.5 h; and
the incubation is carried out in a buffer solution.

10. The sugar-targeting nanoparticle according to claim 3, wherein the targeting molecule and the first linking compound are grafted through esterification reaction, the first linking compound is grafted to an end containing the mercapto group of the first hydrophilic biomaterial, an amino end of the first hydrophilic biomaterial is linked with a carboxyl end of the second linking compound through dehydration condensation, and the cationic compound is linked with the second linking compound through polymerization.

11. The sugar-targeting nanoparticle according to claim 3, wherein the first linking compound is malcimidopropionic acid, the second linking compound is CPADB, and the cationic compound is GUA.

12. The sugar-targeting nanoparticle according to claim 5, wherein the second hydrophilic biomaterial is PEG-NH2, and the second linking compound is CPADB.

13. The sugar-targeting nanoparticle according to claim 5, wherein an end of the second hydrophilic biomaterial away from the second linking compound is modified with a blocking group.

14. The sugar-targeting nanoparticle according to claim 5, wherein the non-targeting nanocarriers comprise a non-targeting fluorine-containing nanocarrier.

15. The sugar-targeting nanoparticle according to claim 5, wherein the hydrophobic block is FPMA; and the cationic compound is GUA.

16. The sugar-targeting nanoparticle according to claim 15, wherein a molar ratio of the product after the dehydration condensation reaction, the GUA and the FPMA added in the copolymerization reaction is 100-110:1800-2000:1.

17. The sugar-targeting nanoparticle according to claim 6, wherein the molar ratio of the targeting nanocarriers to the non-targeting fluorine-containing nanocarriers is 2.5:7.5.

18. The sugar-targeting nanoparticle according to claim 17, wherein a polymerization degree of the GUA is 16-20, and a polymerization degree of the FPMA is 2-6 in the non-targeting fluorine-containing nanocarriers.

19. The sugar-targeting nanoparticle for modifying siRNA according to claim 8, wherein a mass ratio of the non-targeting fluorine-containing nanocarriers to the siRNA is 1.5-5:1.

20. The sugar-targeting nanoparticle for modifying siRNA according to claim 19, wherein the mass ratio of the non-targeting fluorine-containing nanocarriers to the siRNA is 2.5:1.

* * * * *